United States Patent [19]

Schram

[11] Patent Number: 4,743,361

[45] Date of Patent: May 10, 1988

[54] MANIPULATION OF PARTICLES

[75] Inventor: Cornelius J. Schram, Bedford, England

[73] Assignee: Internationale Octrooi Maatschappij "Octropa" BV, Rotterdam, Netherlands

[21] Appl. No.: 751,736

[22] PCT Filed: Oct. 31, 1984

[86] PCT No.: PCT/GB84/00368

§ 371 Date: Jun. 20, 1985

§ 102(e) Date: Jun. 20, 1985

[87] PCT Pub. No.: WO85/01892

PCT Pub. Date: May 9, 1985

[30] Foreign Application Priority Data

Oct. 31, 1983 [GB] United Kingdom .................. 8328990
May 11, 1984 [GB] United Kingdom .................. 8412148

[51] Int. Cl.⁴ .............................................. B03B 5/00
[52] U.S. Cl. ........................................ 209/1; 209/155; 209/158; 210/243; 210/748
[58] Field of Search ................... 209/1, 638, 132, 155, 209/158, 159; 210/748, 243; 55/277; 181/231; 406/168

[56] References Cited

U.S. PATENT DOCUMENTS

| | | | |
|---|---|---|---|
| 2,300,761 | 11/1942 | Amy | 183/1 |
| 3,826,740 | 7/1974 | Jewett | 210/748 |
| 4,055,491 | 10/1977 | Porath-Furedi | 210/748 |
| 4,276,913 | 7/1981 | Szonntagh | 73/864.81 |
| 4,280,823 | 7/1981 | Szonntagh | 209/1 |
| 4,523,682 | 6/1985 | Barmatz et al. | 209/638 |
| 4,673,512 | 6/1987 | Schram | 210/748 |

FOREIGN PATENT DOCUMENTS

| | | |
|---|---|---|
| 836640 | 5/1952 | Fed. Rep. of Germany . |
| 3218487 | 11/1983 | Fed. Rep. of Germany . |
| 828204 | 5/1938 | France . |
| 8401527 | 4/1984 | World Int. Prop. O. .............. 209/1 |
| 713272 | 8/1954 | United Kingdom . |
| 2059796 | 4/1981 | United Kingdom . |
| 2098498 | 11/1982 | United Kingdom . |

OTHER PUBLICATIONS

*IBM Technical Disclosure Bulletin,* "Utransonic Continuous Flow Plasmapheresis Separator", H. W. Curtis &, E. J. Stephans, vol. 25, No. 1, Jun. 1982.

*Mining Engineering,* "Ultrasonic Desliming and Upgrading of Ores", S. C. Sun and D. R. Mitchell, Jun. 1956, pp. 639–644.

Primary Examiner—Robert B. Reeves
Assistant Examiner—Donald T. Hajec
Attorney, Agent, or Firm—Cushman, Darby & Cushman

[57] ABSTRACT

Separation of particles types from a mixed population of particles in a liquid is obtained in an ultrasonic wave produced by interference between the outputs from spaced ultrasonic sources (115,118). One or more selected particle types may be separated by displacement axially along the standing wave or may be carried transversely through the standing wave or by combining both methods. The described separation can be achieved by control of flow of the liquid or giving the standing wave a drift, or by controlling the intensity or the frequency of the standing wave or by any combination of these factors. The preferred ultrasonic frequency range is between 100 kHz and 100 MHz. The process is particularly suitable for the separation of biological particles, from macromolecules to plant cells.

13 Claims, 6 Drawing Sheets

CONTENTS OF VESSEL 122

| SIZE GROUP | PERCENT |
|---|---|
| 3·6 | 9·0 |
| 4·5 | 19·6 |
| 5·7 | 23·2 |
| 7·2 | 12·9 |
| 9·0 | 21·9 |
| 11·4 | 12·4 |
| 14·3 | 0·9 |
| 18·1 | — |

CONTENTS OF VESSEL 127

| SIZE GROUP | PERCENT |
|---|---|
| 3·6 | 5·4 |
| 4·5 | 4·9 |
| 5·7 | 4·3 |
| 7·2 | 5·7 |
| 9·0 | 39·9 |
| 11·4 | 36·6 |
| 14·3 | 2·2 |
| 18·1 | 1·0 |

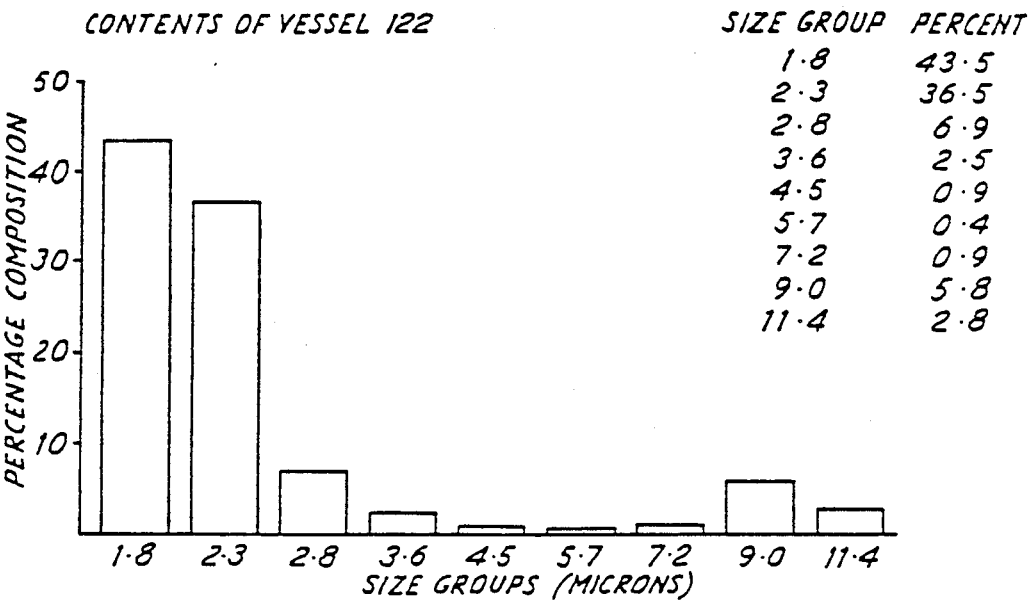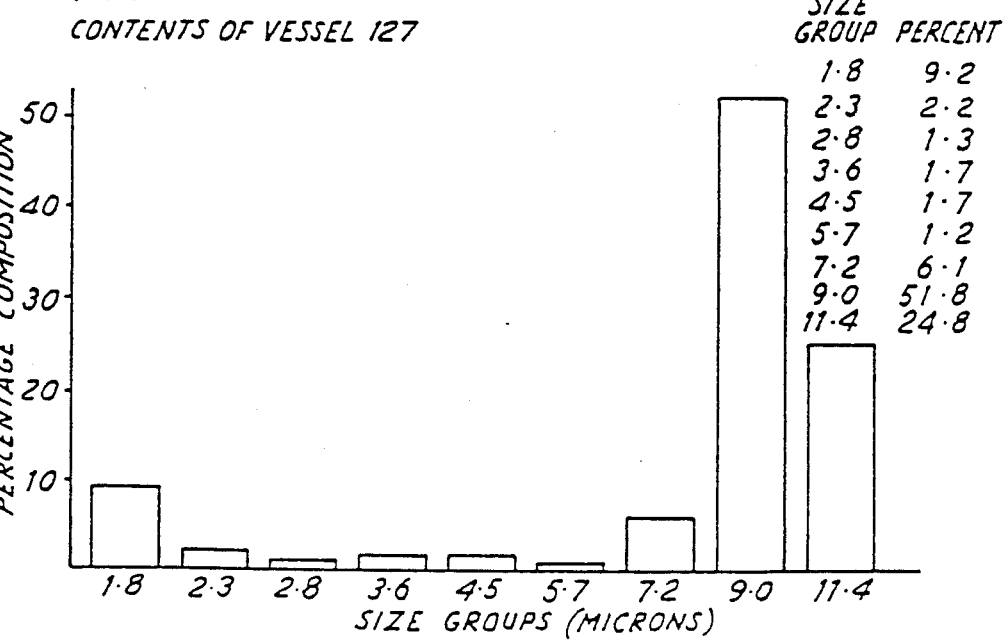

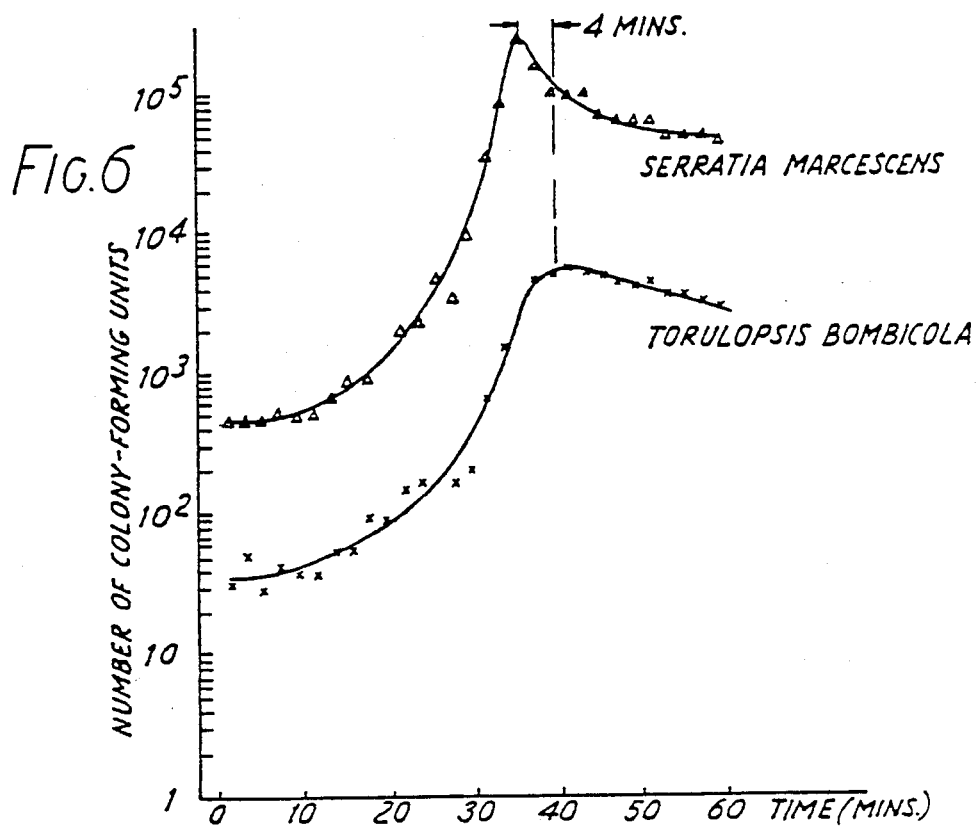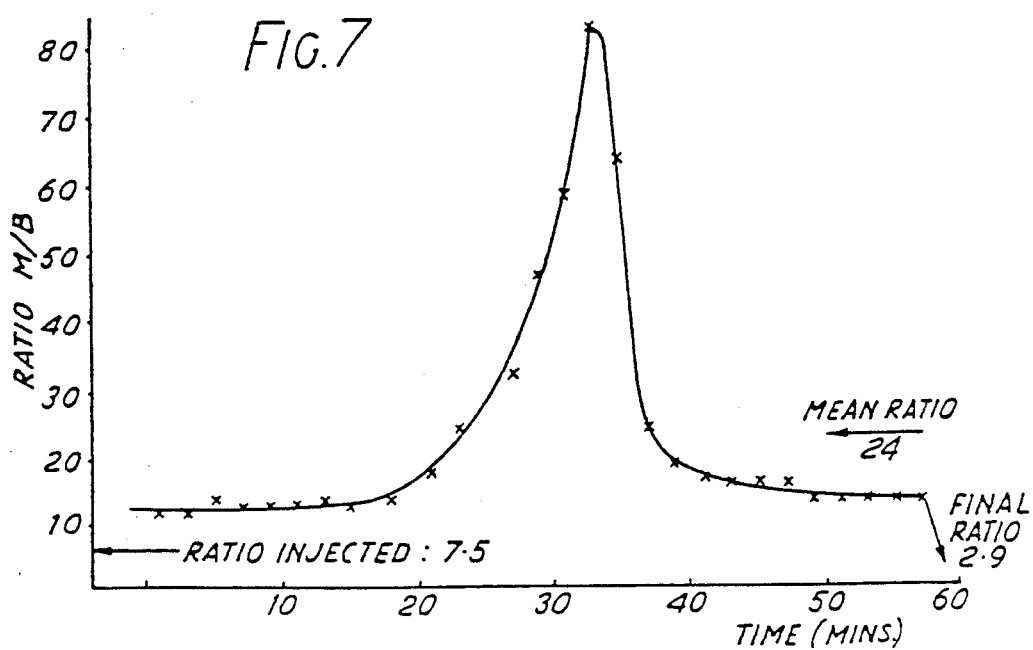

MANIPULATION OF PARTICLES

The present invention relates to the manipulation of particulate matter in a fluid medium by the use of ultrasonic wave energy, and in particular for the separation of particles, including the segregation of dissimilar particles from a mixture of particles in a fluid, whether for example for concentrating particular types of particle or for finely separating or "chromatographing" particulate matter.

The use of standing waves generated by low (sonic) frequency sources in a fluid medium has been proposed for separating particulate matter by precipitation, for example in U.S. Pat. Nos. 2,300,761 and 3,826,740 and WO No. 84/01527. In U.S. Pat. Nos. 4,276,913 and 4,280,823 there is described the use of a transducer emitting an ultrasonic frequency signal of relatively low frequency (150 kHz) to produce a standing wave in a gaseous medium as an aid to the manipulation of particles for gas column chromatography.

In U.S. Pat. No. 4,280,823 the transducer is positioned at one end of a hollow gas-filled tube and is reflected back from the opposite end. Along the same axis the interference between the incident aand reflected waveforms produce a standing wave that is said to function as the plates of a conventional chromatographic column, as is known for molecular separation, by retaining different size molecular particles at the nodes of the wave pattern for different times. In an instrument described in this disclosure, the standing wave pattern is generated in a vertical gas column into which a sample of body fluid components, such as blood cells or bacteria, are injected to be transported by the combined effects of gravity and the carrier gas flow through the column and past a detector for detecting the passage of constituents of the sample which have undergone some degree of separation by the standing wave pattern. The standing wave is produced by tuning the generator driving the transducer to a resonant frequency of the column length so that interference between the emission from the transducer and the reflection from the opposite end of the column produces a stationary pattern of nodes and antinodes.

Such an arrangement is subject to many practical limitations, such as the difficulty of injecting a particulate sample into a gas stream, the difficulty of controlling the separation rate in the carrier gas flow while maintaining the particles suspended therein, and the practical impossibility of achieving a measurable separation between sample components that act very similarly to external forces, such as gravity, upon them.

U.S. Pat. No. 4,280,823 suggests that the wave frequency can be changed to control the resolution of the column, (i.e. altering the distance between nodes or "plates") and if the wavelength is small in relation to the column length there would be a number of discrete resonant frequencies. It is also suggested that a nonresonant mode can be employed, although with a loss of efficiency, but unless there is resonance the transducer emission will then be unable to produce a standing wave pattern. Control of the separation of the constituents of a samaple is thus limited in practice to varying the introduce undesirable secondary effects. Any control of selectivity by change of frequency must be limited to a relatively small number of discrete steps if the standing wave pattern is to be maintained.

In U.S. patent application No. 29,112 of 1982 by Barmatz et al (NASA NPO 15559-1) there is described an apparatus for the separation of particles of different types as they pass along the length of a horizontal chamber. An acoustic transducer at one end of the chamber operates at a resonant frequency of the chamber to generate a standing wave with a wavelength that is half the height of the chamber. This results in a so-called force potential well in the mid-height region of the chamber, in which the particles will tend to concentrate. The particles are also subjected to an external force, in particular gravity, acting transversely to the flow and there is some separation within the well depending upon the reactions of particular particle types to the acoustic energy force and the additional transverse force, so that the different particle types tend to settle at different heights within the force potential well, or if the influence of the transverse force is sufficiently strong they fall to the bottom of the chamber because the acoustic energy force falls off rapidly once the particle has fallen more than half way between the centre of the well (a node) and the antinode below. Such an arrangement can give only a crude form of separation. In the case of particles suspended within the force potential well, the separation between the different types will inevitably be very small and their positions will be influenced by a number of transient conditions, such as fluctuations in the flow along the chamber so that precise and consistent separation of a number of particle types is impossible.

There may also be mentioned GB 2 098 498A in which there is described a method of displacing contaminating particles in a flow of lubricant to bring them towards a magnetic collector, by the use of two opposed ultrasonic sources controlled in phase so as to generate a standing wave that drifts across the flow. In this apparatus there is no discrimination between different types of particles, e.g. as regards size or morphology, that are influenced by the standing wave, although it can be expected that the flow will carry with it a wide variety of small particles, and it is therefore the use of a magnetic collector that will itself effect the separation of magnetically influenced particles as a selected group.

According to one aspect of the present invention, there is provided a method of separating one or more particle types present in particulate matter in a liquid column, which by interference between the outputs of spaced ultrasonic energy sources a standing wave is established with wave fronts extending transversely in the column, said separation being obtained by controlling the rate of liquid flow and/or the rate of drift of the standing wave along the column, and/or by controlling the intensity and/or the frequency of the standing wave pattern in the column.

According to another aspect of the invention, there is provided apparatus for separating one or more particle types present in particulate matter and comprising, a liquid column, means for admitting the liquid and said matter into the column, spaced ultrasonic energy sources for directing ultrasonic wave outputs into the liquid column to generate by interference between their outputs a standing wave with transversely extending wave fronts in the space occupied by said liquid and matter, and for said separation of the or each specific particle type there are provided means for controlling the amplitudes of the outputs of the two sources so as to match their interferring outputs and vary the intensity of the standing wave, and/or mass for controlling the relative phase of the outputs so as to hold the standing wave fixed or to produce an adjustable rate of drift of said wave along the column.

According to a further aspect of the invention, there is provided apparatus for separating one or more particle types present in particulate matter, and comprising a column arranged to be filled with a carrier liquid flow and having entry and exit stations spaced along its length for the passage of said particulate matter, spaced ultrasonic energy sources arranged to transmit ultrasonic wave energy through the column to establish a standing wave between said entry and exit stations with wave fronts extending transversely in the column, and wherein for performing saida separation there are provided means for control of (i) the rate of carrier liquid flow through the column, and/or
(ii) the relative phase of the energy outputs of the sources to hold the standing wave stationary or cause it to drift along the column, and/or
(iii) the amplitudes and/or the frequency of the energy outputs of the sources.

In such apparatus there may be a uniform flow of the carrier liquid from an entry at one position on the length of the column to an exit at another position spaced therefrom. It is possible, however, to provide more than one entry and/or exit at spaced positions, by means of which different interactions with the standing wave in the column.

According to a still further aspect of the invention, there is provided a method of separating at least one particle type present in particulate material in a liquid-filled space by means of at least one ultrasonic standing wave established by interference between the outputs of spaced ultrasonic energy sources, said separation being obtained in said standing wave by controlling the rate of liquid flow and/or the rate of drift of the standing wave, and/or by controlling the intensity and/or the frequency of the standing wave, and said at least one separated particle type being removed while suspended in a flow of liquid through an outlet from said space.

The present invention also relates to a method for selectively segregating different particle types in a mixed population of particle types suspended in a fluid medium (liquid of gaseous) wherein the fluid medium is passed through a zone in which an ultrasonic standing wave is established such that the direction in which the fluid medium moves has a component normal to the direction of the standing wave and the frequency and/or the amplitude of the standing wave and the velocity and/or the direction of flow of the fluid medium and/or the rate at which the standing wave is caused to drift are controlled such that one or more particle types are segregated and carried out of the zone containing the standing wave by the fluid flow, whereby the different particle types are continuously collected as separate populations or particle types at different locations.

According to yet another aspect of the invention, there is provided an apparatus for separating one or more particle types carried in a fluid flow comprising a flow chamber, spaced ultrasonic sources arranged to establish a standing wave therein by interference between their outputs, means for controlling said sources so as to produce drifting of the standing wave along its axis, fluid inlet and outlet means for the fluid flow carrying said particles, said inlet and outlet means being disposed relative to said standing wave such that the fluid in the chamber flows through said standing wave transversely to the axis thereof, the exit means comprising at least two openings that are spaced in the direction of said axis whereby particles of the or each chosen type, in depending upon their displacement relative to the fluid imposed by the standing wave energy, are delivered to a predetermined opening.

The standing wave pattern results from the superimposition of the progressive wave outputs of the two sources, the standing wave occurring in the area of overlap of the two progressive wave patterns whether or not the axes of propagation of the outputs from the two sources are coincident. If the two opposing progressive waves differ in amplitude the net effect is a standing wave upon which is superimposed a progressive element. In practice this will almost always arise to some degree due to the attenuation of the waves in the fluid medium (although at frequencies up to the order of $10^2$ MHz it is possible to balance the amplitudes to produce operating zone of useful length in which progressive wave components are negligibly small and in some special cases higher frequencies may be applicable). If the two progressive waves differ slightly in frequency, the standing wave will drift towards the source emitting the lower frequency. If the two opposing waves differ both in frequency and in amplitude a combination of these effects will be observed, and by means of the control of the sources each effect can be regulated to achieve the desired result.

As a means for separating dissimilar particles in a mixed population, the invention utilises a phenomenon which we shall term herein as "nodal delay". A particle suspended in a liquid nad located in a drifting standing wave will move with the nodes of the standing wave if the acoustic forces predominate, whereas if subject to Stokes forces due to movement of the liquid and these viscous drag forces predominate it will move with a mean velocity equal to the liquid velocity. If the peak acoustic forces are almost exactly balanced by the non-acoustic forces, the particle will move at times with the same velocity as the nodes, and at other times will move with a complex oscillating motion in which, however, the standing wave does not impart any net motion to the particle. In practice the acoustic energy density of each part of a nodal array will not be exactly equal, nor may it be possible to have non-acoustic forces with a constant magnitude in every part of a system. The particle may be subject to Brownian motion which at one moment may augment the acoustic forces and at another moement may augment the nonacoustic forces. For such reasons, when the opposing forces are nearly in balance, a given particle will at one moment move with the standing wave but at another moment will not move with the wave.

The "nodal delay" is the sum of all those times during which the given particle is not moving with the wave. Thus, if the tendency of a given particle type to mass at the nodes overrides totally the effect of the opposing forces in the fluid medium, the nodal delay then experienced by that particle type is zero. If the tendency of a given particle type to remain at the nodes is overriden totally by the effect of the opposing forces, the nodal delay experienced by that particle type can be said to be infinite. Nodal delays having intermediate values arise only when the acoustic and the non-acoustic forces are nearly in balance.

The detailed theory underlying the observed phenomenon of standing waves and their effect of particles in fact is not fully understood. In the following discussion of the mechanism of separation it is indicated that the particles influenced by a standing wave will tend to accumulate at the nodes of the wave but any lack of theoretical understanding has no bearing on the practical application of the invention. Unless stated otherwise, the term "nodes" is used herein may thus be considered to include both nodes and antinodes, because in practice it does not appear to matter to the results that can be achieved.

Considering in more detail the acoustic forces acting on a particle that is small compared to the wavelength of a stationary standing wave having no progressive element, if these forces predominate they urge the particle to the nearest node (in this explanation, those stations along the axis or propagation which the adjacent net acoustic forces act towards are termed nodes and those which said acoustic forces act away from are termed antinodes). Thus in the absence of any applied opposing force, the particle moves to the node at a velocity proportional to the magnitude of the net acoustic force on it at any instant—i.e. the particle reaches a maximum velocity when at an intermediate point between a node and an adjacent antinode.

Suppose now that there is an opposing force from the relative movement of a liquid axially to the standing wave at a constant velocity, the force being less than the maximum acoustic force at that intermediate point. The equilibrium position of the particle is no longer coincident with the node but is displaced somewhat downstream, although it still remains attached to the force field of the node. If the opposing force becomes larger (the velocity increases), so that it exceeds the maximum acoustic force, the particle is swept through the standing wave, accelerating as it nears a node and slowing after it has passed the node, with the result that the particle mean velocity is the same as if no standing wave were present. Thus, a particle is either held on a node or it travels at a mean velocity which is substantially identical with the velocity of the fluid.

If two different particles are considered having different acoustic responses, under influence of the opposing force they will move to different positions of displacement from a node while they are held by the standing wave. As the opposing force is increased, so one particle will be released while the other remains held, so that particles of two different types can thereby be separated axially.

Using an axial opposing force such as the viscous drag of a liquid, in one extreme condition, the position of the standing wave is ficed (i.e. the array of nodes forming the standing wave is at least substantially motionless relative to the sources generating the standing wave) and the carrier liquid flows through the standing wave. In this condition the nodes of the standing wave can be likened to a series of filters or grids through which the particles in the liquid have to pass as they are carried along by the stream. By changing the characteristics of the outputs from the sources, the attraction of different particles to the nodes can be varied, and by appropriate control it is possible, for example, to hold different particle types at the nodes while allowing others to be displaced by the liquid flow. At the alternative extreme, with the liquid stationary and the standing wave caused to drift along its axis, the nodes of the standing wave can be likened to a comb that is passed through the liquid medium and tends to sweep particles with it. It will be understood that be combination of the movements of both the liquid and the standing wave, as well as by controlling the standing wave intensity and/or frequency, it is readily possible to achieve an extremely wide degree of control.

In the above discussion the forces act in a direction parallel to the axis of a standing wave but this is not the only form of force field which may be concerned. The present invention also comprises an arrangement in which there is a component of fluid flow normal to the axis of the standing wave, in an extreme case the fluid flow being substantially at right angles to the standing wave axis. It is therefore necessary to consider also the effect of forces acting normal to the axis of the standing wave.

A particle influenced by the standing wave will not only move towards a node but because the acoustic energy density in the nodal plane will generally not be uniform, it will move parallel to the plane in the direction of increasing energy density. The energy density gradient in the plane of the node is very much smaller than the gradient axially of the standing wave, especially at the ultrasonic frequencies used in the present invention. It can thus be displaced parallel to the nodal plane by a much smaller non-acoustic force. The work done to remove the particle axially from a node to an adjacent antinode is however the same as removing it parallel to the nodal plane, the displacement required parallel to the nodal plane being much greater than the displacement from a node to an adjacent antinode. It is therefore easier to detach a particle from a standing wave by a liquid flow normal to the axis of the wave than by an axial flow relative to the standing wave.

Under practical conditions, the velocity with which a particle moves in the plane of a node is not always the same as the liquid flow velocity in this direction; the particle will accelerate as it moves up an acoustic energy density gradient and will slow in a decreasing gradient. As described with axial movement, however, the average velocity is that of the velocity of the carrier liquid in the plane of the node, unless the particle is held by the node at some local high acoustic energy density region fro which the Stokes forces cannot dislodge it for a time. Finite nodal delays therefore can operate in directions both along and transverse to the axis of the standing wave.

To explain the transverse separation process, consider a uniform liquid flow normal to the axis of a drifting standing wave in a simple case in which the acoustic energy density in each nodal plane can be regarded as substantially uniform. Because there would be no acoustic energy density gradient in the nodal plane, a particle moving with a node will also have a component of movement at the liquid flow velocity, so that if the wave and liquid velocities are the same, the particle will move in a direction at 45° to the standing wave axis. If the wave velocity increases or the amplitude of the wave is reduced, a stage will be reached of near balance between the acoustic and Stokes forces in the axial direction such that the particle slips back to a following node from time to time. The nodal delay thus becomes finite and the mean track of the particle now has a greater inclination to the standing wave axis. At one extreme, when the acoustic forces are completely overriden the angle becomes 90°. At the opposite extreme, if the acoustic forces predominate, e.g. because the liquid flow is so slow, the smallest variations in the energy density of the nodal plane will hold the particle because it cannot pass a local gradient and the track of the particle will thus be axial. It should be understood that in this analysis gravitational forces are assumed to have no significant effect.

It is thus apparent that particles having different transverse nodal delays will move along different tracks to emerge from the standing wave in different positions along the length of the wave. For completeness, it should be mentioned that the nodal delay experienced in this transverse flow case will be composite of the transverse nodal delay and the previously described axial nodal delay.

In respect of the influence that the standing wave will exert on different types of particles within a liquid to collect at the nodes, there will be a relationship between the physical properties of the particles involved and the wavelength and energy of the standing wave. A primary physical property of the particles that may determine this relationship is their size. Many other factors come into consideration however, and for example, particles of similar maximum dimensions, but differing in density or shape will exhibit differing tendencies to accumulate at the nodes.

The invention may be used for the analysis and separation of a very wide size range of particles. Among examples of suitable biological particles there can be considered animal cells, for instance mammalian cells. Thus, it is possible to employ the method to distinguish between red blood cells (7 microns) which have a density of 1.09 gm/cc and are disc shaped, and reticulocytes which are immature red cells (5 microns) and have a distinctive internal structure and acoustic character, and other blood particulates such as neutrophils (10 microns), monocytes (14–20 microns) and lymphocytes (10 microns). Other suitable biological particles for treatment are plant cells (typically 20–30 microns), microorganisms (a typical coccus being about 1–2 microns in diameter while a bacillus is rod-shaped about 2–3 microns long), and spores of microorganisms which are much denser (specific gravity 1.3) than when in the vegitative state. Cell constituents such as nuclei, mitachondria and microsomes are further examples of biological particles that can be treated using the method of the present invention, and as further instances may be mentioned plankton, yeasts, pollen, protozoa, richetsia and viruses.

Outside the field of biological particles, the method of the invention can be employed for the manipulation of many industrial particulates, including dispersions, suspensions and finely-divided pricipitates. As examples can be mentioned clays (the plate-like hydrous aluminium silicate particles which range in size from colloidal to 4 microns), cement (the particles of Portland cement are ground to sizes mostly below 10 microns), paint pigments (titanium dioxide may be used in particles about 0.3 microns in diameter), as well as dusts, such as coal dusts and asbestos.

The upper size limit for manipulation of particles by the method of the invention is determined by the internodal distance in the standing wave. Acoustic forces on the particles essentially cease to be effective when the particle is so large that it spans the distance between a node and the adjacent antinode. In water at NTP, with directly opposed ultrasonic sources at 100 kHz, this distance is about 3.5 mm.

The lower limti to size is more difficult to specify because of the number of factors involved and requires to be determined experimentally in any particular case. It appears that one factor is the size of particles relative to the internodal distance, because the efficiency of separation falls as the difference between these dimensions increases.

For the types of particles referred to above, the optimum frequency needed to establish an appropriate standing wave in water will be in the range 100 kHz to as high as 250 MHz, or more usually 100 MHz. In the upper end of this range it is necessary to consider the reduction of intensity of the ultrasonic radiation with distance from the source: such attenuation means that the two progressive waves cannot be identical in amplitude except in a very small region and in practice the stainding wave will include a minor progressive component. The use of liquid, e.g. water, as a carrier medium enables such frequencies to be employed without undue attenuation and a useful operating zone extends to both sides of the position of energy balance; for example, at 1 MHz the intensity of a propagated wave is halved only after travelling 13.8 meters aand at 5 MHz the corresponding figure is 0.55 meters. For many practical purposes it is only necessary to establish the standing wave over much smaller distances. Using the example of directly opposed sources operating in water, at 100 MHz, the distance between a node and an adjacent antinode is about 4 microns, but this should still allow large macromolecules with molecular weight in the region of $10^6$ Daltons (equivalent to a sphere of about 0.005 microns diameter) to be separated. The working distance will of course be small due to the attenuation at that frequency, but an axial length of 1 mm (133 nodes) may be available.

The use of water has an advantage in that it is a benign medium for biological particles generally. In addition, in some instances it is an advantage to be able to choose a medium with a density not widely different from those of particulate materials required to be separated, so that gravitational effects can be minimised and sensitivty to the differences between particle types is improved. At higher frequencies there are also the advantages of a reduction of beam spread and the ability to use higher powers without risk of cavitation. It has been found, moreover, that the efficiency of association of particles with nodes increases with frequency.

While in most cases water is the most appropriate medium it may be advantageous to increase the density of the liquid by the addition of solutes such as sources, or to control osmotic effects, or to increase viscosity by the addition of suitable macromolecular materials. Polar liquids having a lower density than water, such as methyl alcohol, may be useful carrier liquids for some particulate materials, while for the analysis of substances sensitive powders such as cements, non-polar liquids such as kerosene would be chosen. In other cases it may be advantageous to use oils having a higher viscosity and lower density than water. It will be understood that the different characteristics of such diverse liquids will be a factor in determining the frequencies of the ultrasonic sources employed.

It should also be understood that the invention may be embodied in applications in which the carrier liquid has a higher density than the particulate material. Thus, a high densiy mobile liquid such a bromoform may be suitable to some particular cases. As further possibilities, it will be appreciated that the method of the present invention can be operated at temperatures both considerably higher and lower than room temperature, and the static pressure may also be controlled, so that substances normally solid or gaseous at normal temperatures and pressures can also be considered as carrier liquids. In the case of inorganic particles, it may be preferred to use liquid carriers other than water, e.g. for density considerations or in order to ensure that the particulate material is dispersed.

As will be understood by the preceding explanation of nodal attachment, in a closed system with a standing wave established in a fluid and fine particles suspended in the fluid, the net free energy of the system is reduced as the particles collect at the nodes. The degree to which the net free energy of the system is reduced as a particle moves to a node, and conversely the work which needs to be done in order to remove the particle from the node, depends on the acoustic properties of the particle, that is, its shape, size, density, compresibility, rigidity and general physical internal structure, the properties of the fluid, e.g. its density and the speed of sound in the fluid, and the intensity and frequency of the ultrasonic standing wave.

Work done in moving a particle from a node increases as the amplitude of the standing wave increases. It also increases as the frequency increases, but if the wavelength becomes so short that the magnitude of the distance between a node and an adjacent antinode approaches the size of the particle, the work done in moving the particle from the node will reduce.

The tendency of the wave to accumulate particles at its nodes can be opposed by a wide variety of means in order to counterbalance, wholly or partially, the forces exerted on the particles due to the standing wave, so creating a situation in which motion of the particles can be controlled. Relative motion between the fluid medium supporting the particles and the standing wave as already described provides an important means of control, but in general the controlling influences may include further external forces, e.g. electromagnetic or electrostatic or centrifugal or gravitational force fields, and these can be controllably combined to determine the rate and degree of separation. For example, red blood cells carry a charge and in an electric field they therefore have acting on them a force proportional to the product of the charge and the electric field strength. This force could be used to oppose the acoustic forces holding a red blood cell in a standing wave. Variation of the energy intensity of the standing wave and/or its frequency provides further means of control.

The invention will be described by way of example with reference to the accompanying drawings in which:

FIGS. 2 to 7 show a chart and tabular form some experimental results obtained with the apparatus of FIG. 1.

Figure 1:
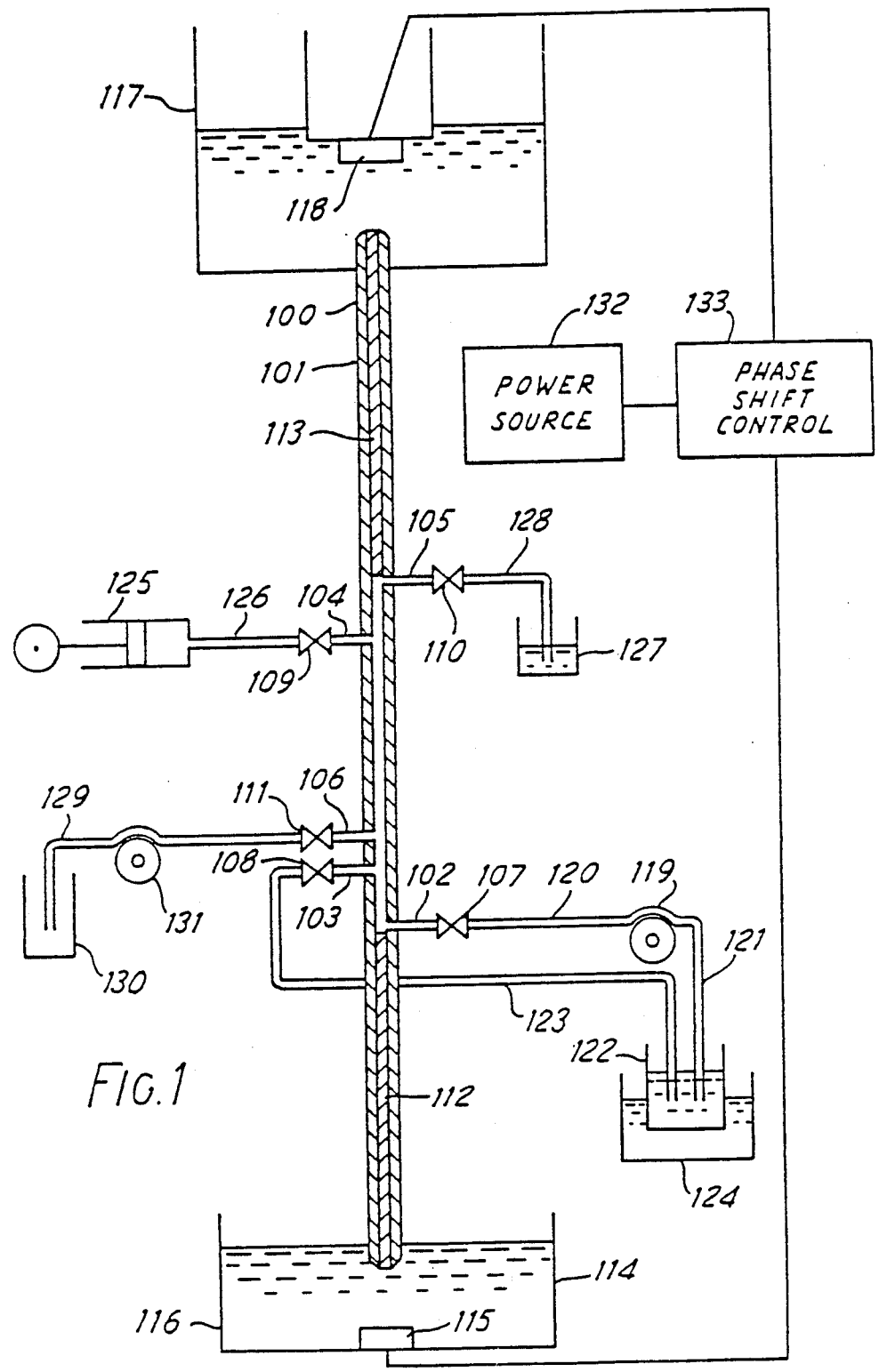
FIG. 1 is a diagrammatic illustration of a particle segregating apparatus according to the invention.

Referring to FIG. 1, the apparatus comprises a vertical column 100 formed from a glas tube 101 having a bore 2.5 mm diameter and an external diameter of 7 mm fitted with access ports, 102, 103, 104, 105 and 106. These ports comprise small stainless steel tubes having a bore of 1 mm diameter and having ends flush with the internal bore of tube 101. Each port has a 0.5 mm bore silicone rubber connecting tube provided with a pinch valve 107, 108, 109, 110 and 111 respectively.

Gelatine plugs 112, 113 respectively are cast into the section of tube 101 between the bottom of port 102 and the base of the column 100 and between the top of the port 102 and the base of the column 100 and between the top of the port 105 and the top of the column 100. These plugs of 10% w/w gelative in water have been hardened with formaldehyde and form low attenuation acoustic windows having an ultrasonic impedance very similar to water.

The lower end of column 100 dips into water contained in a vessel 114 in which there is a 10 mm diameter barium titanate pizeoelectric transducer 115 having a resonant freuqency of 2.02 MHz. The transducer 115 is mounted inside the vessel 114 on a horizontal base 116 with its centre in line with the vertical axis of the column 100 and with the transducer transmitting face normal to this axis.

The upper end of the glass tube 101 projects into a vessel 117 and is in contact with water contained in the vessel. A second 10mm diameter barium titanate transducer 118 having a resonant frequency of 2.02 MHz is positioned such that the centre line of transducer 118 coincides with the centre line of the glas tube 101, and the transmitting face of transducer 118 dips into the water in vessel 117 and is normal to the centre line of glass tube 101. Each transducer 115, 118 has an impedance of about 50.

Means are provided (not shown) to set and maintain the alignment of transducers 115 and 118 coaxial one with the other and with their transmimtting faces parallel. Means are also provided (not shown) for transverse and angular adjustment of the tube 101 to set the axis of the column 100 coincident with the common axis of the transducers 115 and 118.

A peristaltic pump 119 is connected by 0.76 mm bore plastic tubes 120, 121 to the port 102 via valve 107 and to a vessel 122. Similar small bore plastic tubing 123 connects the distal end of valve 108 to the contents of vessel 122. A minature ultrasonic bath 124 contains vessel 122 and provides agitation to the contents of the vessel. A motorised syringe 125 is connected via the valve 109 to the port 104 with similar bore plastic tubing 126. The valve 110 connects the port 105 to a vessel 127, also via small bore plastic tubing 128. Similar tubing 129 connects the valve 111 to vessel 130 via a peristaltic pump 131.

To power the transducers a power source 132 is connected to a phase shift control arrangement 133 whereby two electrical driving outputs are produced with a progressive change of phase between them, whereby the interaction of ultrasonic outputs from the opposed transducers in the column produce a standing wave pattern having a relative slow drift towards the lagging phase output.

In a preferred method of achieving the progressive wave change there is utilised a Wavetek Model 186 Phase Lock Sweep Generator which is able to produce an output in predetermined phase relationship to a reference input voltage, in dependence upon the application of a dc bias voltage. The two transducers are driven, one by the reference voltage and the other by the phase-controlled output voltage. A microprocessor is programmed to produce a cyclic stepped output that controls the bias voltage, so that the phase difference between the reference voltage and the phase-controlled output voltage change in progressive steps to produce a series of momentary frequency differences that result in drifting of the standing wave. The rate of drift is determined of course by the magnitude and frequency of the changes of reference voltage as set by the microprocessor programme.

The operation of the apparatus will be illustrated in the following examples.

EXAMPLE 1

Polystyrene divinyl microspheres having a density of about 1.05 grams per ml. and a known size distribution were separated into fractions having different size distributions using the apparatus described above.

Clean, particle-free water was placed in vessel 122 and pumped by pump 119 via valve 107 into the column 100 and out via port 105 to fill completely the space between the plugs 112, 113. Care was taken to ensure that no small bubbles remained in the column. Clean water was also expressed by the motorised syringe 125 via valve 109 to displace all air but thereafter the valve 109 was closed. When the column was completely filled with water, the water in vessel 122 was replaced by the segregation sample consisting of 10 ml of an aqueous suspension of $3.3 \times 10^7$ microspheres having a diameter of a few microns.

With the transducers 115, 118 and the glass tube 101 aligned as already described, the transducers were energised at 55 volts and by the driving outputs, the voltage applied being adjusted to produce equal acoustic outputs from the transducers. A standing wave was thus formed throughout the bore of the glass tube 101. The phase shift control arrangement was so adjusted that the standing wave pattern progressed upwards at a velocity of 50 mm per minute.

The apparatus was operated with valves 111 and 110 closed. The suspension of particles contained in vessel 122 gently agitated by the ultrasonic bath 124 was drawn by the pump 119 through valve 108 into port 103 to flow down the column and return to the vessel via port 102, valve 107 and tubing 120 at a rate of 0.77 ml per minute in the return to the vessel 122. The working length of the column between the ports 102, 103 is about 10 mm. At the same time, the motorised syringe 125 was operated to drive water down the column via valve 109 and port 104 at a rate of 0.1 ml per minute, to join the flow of suspended particles in the tube 120 into vessel 122.

A liquid flow was thus established having an average velocity of 20 mm per minute down the tube 101 between ports 104 and 103 and a velocity of 180 mm per minute between ports 103 and 102. Since the standing wave was moving up the column at 50 mm per minute, the mean relative velocity between the water and the standing wave was 70 mm per min. between ports 104 and 103 and 230 mm per minute between ports 103 and 102.

Polystyrene particles exceeding a specific minimum diameter were collected by the moving nodal array from the junction of the port 103 and carried to the top of the column to collect on the lower face of the upper gelatine acoustic window. The process was operated for 20 minutes when the circulation of the supply of particles to the column was stopped by stopping the pump 119 and the syringe 125. Valves 107 and 108 were closed, valve 111 was kept closed and valve 110 was opened.

Rapid operation of the syringe 125 pumped 1.5 ml of water via port 104 and port 105 into the vessel 127 sweeping out of the column all the particles which had collected at the upper acoustic window.

The numbers and size distribution of the polystyrene particles originally present in vessel 122, those remaining in vessel 122, and those collected in vessel 127 were analysed using a particle size and number analyser (Coulter Counter, model TAII, Coulter Electronics Ltd. Harpenden, England) appropriately calibrated and fitted with a 70 micron aperture.

The size distribution given in terms of the percentage of the total number of particles falling into various size groups is given in Table 1 which shows the change in composition of the population of microspheres in vessel 122 at the beginning and the end of the run and the composition of the population collected in the vessel 127.

TABLE 1

| Size Range Microns | Mean Diam Microns | Composition of Microsphere Population (Percentage) | | |
|---|---|---|---|---|
| | | Vessel 122 | | Vessel 127 |
| | | Initial | Final | |
| 1.59–2.00 | 1.80 | 2.1 | 4.9 | 3.4 |
| 2.00–2.52 | 2.26 | 1.8 | 3.4 | 2.0 |
| 2.52–3.17 | 2.85 | 2.7 | 3.8 | 1.7 |
| 3.17–4.00 | 3.59 | 6.6 | 7.3 | 2.3 |
| 4.00–5.04 | 4.52 | 14.7 | 15.4 | 4.7 |
| 5.04–6.35 | 5.70 | 16.4 | 17.1 | 8.0 |
| 6.35–8.00 | 7.18 | 11.6 | 11.1 | 10.2 |
| 8.00–10.10 | 9.05 | 30.6 | 26.3 | 42.1 |
| 10.10–12.70 | 11.40 | 13.3 | 10.7 | 24.5 |
| 12.70–16.00 | 14.35 | 0.3 | 0.2 | 1.0 |

In vessel 122 the arithmetic means diameter of the population was reduced from $7.15\mu$ to $6.65\mu$ due to the preferential removal of the larger praticles, while the particles collected in vessel 124 had a mean diameter of $8.42\mu$.

RATE OF WORKING

From Table 1 it can be seen that the total size range considered in this example is from $1.59\mu$ to $16.0\mu$. The bulk of this population may be divided into two groups such that:

Group A covers all particles from 3.2 to $8.0\mu$
Group B covers all particles from 8.0 to $12.7\mu$ The number of particles in these two groups found initially in vessel 122 and collected in vessel 127 is shown below in Table 2:

TABLE 2

| | Number of Microspheres | |
|---|---|---|
| | Group A | Group B |
| In vessel 121 | $1.6 \times 10^7$ | $1.4 \times 10^7$ |
| In vessel 124 | $1.1 \times 10^6$ | $2.9 \times 10^6$ |

Group A particles were fed to the drifting standing wave at a rate of 1.2 million per minute, and 55,000 of these lifted to the top of the column per minute, that is 4.5%.

Group B particles were fed to the drifting standing wave through port 103 at a rate of 1.09 million per minute, and 150,000 of these were transported to the top of the column per minute, that is, 14%.

At a frequency of 2 MHz, the internodal distance of the standing wave in water is about 0.35 mm, so at a wave drift of 50 mm per minute, 143 nodes pass per minute. Since the total number of particles collected in vessels 127 was $4.35 \times 10^6$ collected in 20 minutes, 217,500 particles per minute were being transported up the column, that is an average of over 1,500 on each node.

The process may be operated continuously, that is to say, with a continuous supply of fresh material to port 103, the port 105 remaining open to a small scavenging liquid flow that carries separated particles out of the column. It may also be noted that in a discontinuous mode of operation different groups of particles can be collected successively at the port 105, the apparatus being controlled in such a way that the different types of particles in a sample are retained in the column for different periods of time, e.g. by progressive changes of the intensity of the standing wave or of the relative velocity between the standing wave and the carrier liquid so that the nodal delay characteristic of each particle type determines the order in which the respective types reach the port 105.

EXAMPLE 2

Polystyrene microspheres were separated into fractions having different size distributions as for Example 1 and using the apparatus hereinbefore described, but the concentration of particles initially in vessel 122 was only half that in Example 1.

Figure 2:
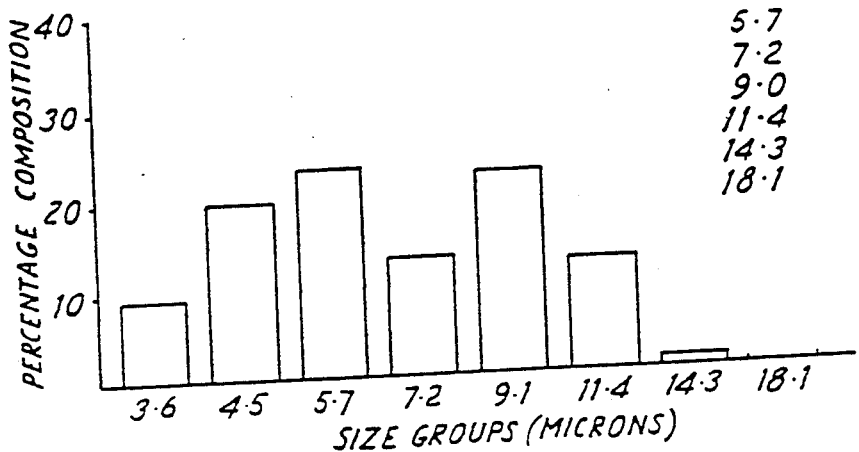
Figure 3:
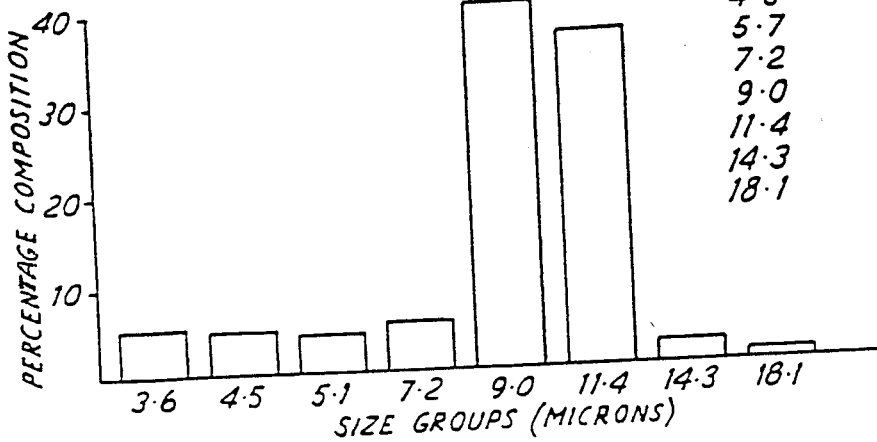

FIG. 2 shows a histogram of the percentage of the total number of particles falling into various size groups in a sample being taken from the vessel 122 at the start of the run, while FIG. 3 shows a similar histogram of the size distribution of particles taken from a vessel 127 at the end of the run. The mean diameter of particles in the vessel 122 at the start of the run was 7.04$\mu$ and that of the particles in the vessel 127 at the end of the run was 9.4$\mu$.

EXAMPLE 3

Using the method of Example 1, the apparatus shown in FIG. 1 was used to test its ability to select quickly and concentrate a small fraction of larger particles about 9 microns in diameter present in a large proportion of smaller particles, about 2 microns in diameter. The analysis of the size of distribution of the initial mixture of polystyrene microspheres placed in the vessel 122 is given as a histogram in FIG. 4, based on a count of 30,000 particles. FIG. 5 is a histogram to the same scale of the size distribution of the particles collected in the vessel 127 after 30 minutes.

It will be seen that in the vessel 122 initially, 91% of the particles were in the size range 1.8 to 4.5$\mu$ while the size range 7.2 to 11.4$\mu$ accounted for 9%. In the vessel 127 at the end of the run, however, only 16% of the particles were in the range 1.8 to 4.5$\mu$ and 84% were in the 7.2 to 11.4$\mu$ group.

The ratio of these two size groups therefore changed from an initial 10 to 1 down to 0.9 to 1, that is, an overall change exceeding 50 to 1. This was achieved in a single pass through a 38 mm length of working column with ultrasonic standing wave patterns drifting at a rate of 50 mm per minute.

These examples illustrate that by the use of the invention, small particles may be separated into different populations consistently and rapidly while travelling only a short distance. Considerable enrichment with respect to a particular selected class is possible with relatively high concentrations of particles.

Adjustment of the velocities of the standing wave and of the counter-flow in the column 101 result in the predicted results. For instance, in a further experiment, the percentage of the particles falling in the size group 14.3 microns increased when the wave drift velocity was increased, while those somewhat smaller decreased. The change in this size group with changing wave velocity at a constant acoustic energy and a constant counter flow in shown in Table 3.

TABLE 3

| Wave Velocity | Size Group (microns) |
| --- | --- |
| | 14.3 |
| 70 mm per min. | 4.5% |
| 90 mm per min. | 5.4% |
| 110 mm per min. | 7.3% |

The apparatus of FIG. 1 can also be employed with circulation of liquid from the vessel 122 through the column from port 102 to port 103, i.e. in the same direction as the wave drift. The velocity of liquid flow then has the same direction and can be arranged to be not far different from the velocity of wave drift. In this flow section therefore, the nodes of the wave pattern are loaded with particles experiencing little if any nodal delay and consequently there is no significant separation of the particles. Opposite the port 103, where the liquid flow exits, the particles reach a local zone in which the relative velocity between the liquid and the drifting wave increases, causing separation of the particles here, with a fraction of larger mean size being carried up the column by the standing wave, while the remainder of the particles return via port 103 to the tank 122.

EXAMPLE 4

This is an example of the separation of a mixture of viable microorganisms without damaging their normal function, using a slightly modified form of the apparatus of FIG. 1. Thus, the vessel 127 is not needed nor is the connection from port 103 to the vessel 122. At the port 103, the pinch valve 108 is repositioned so that a short length of 0.5 mm bore silicone tubing connects the valve to the port 103, sufficient to allow the needle of a hypodermic syringe (not shown) to pierce the tubing wall and pass through the bore of port 103 to enter the bore of tube 101.

A bacterium, *Serratia marcescens* (NCTC 1377) and a yeast, *Torulopsis bombicola* (PRL 123-64) both in the late stationary phase of growth, were mixed and diluted insterile 0.1% peptone water (available commercially from Oxoid Co. Ltd) acting as a carrier fluid.

With the tube 101 completely filled with sterile 0.1% peptone water, this suspension of microorganisms was loaded into a 5 ml hypodermic syringe fitted with a long needle and the needle was passed through the wall of the tubing connected to the port 103, and through that port to inject 40 microliters of the suspension into the base of the filled tube 101. This injected suspension of microorganisms occupied about an 8 mm length of the tube 101 adjacent to port 103. Whilst the sample was being loaded into the column, valves 107, 108, 109 and 111 were closed and valve 110 was opened to allow displaced peptone water to leave the column.

With valve 107 then opened, the transducers 115 and 118 were energised at 2 MHz and 50 volts and the resultant standing wave was held stationary or nearly so e.g. with a downwards drift of 1 mm per minute, while sterile 0.1% peptone water contained in vessel 122 was pumped through port 102 at an average velocity in the bore of the tube 101 of 4 mm per minute. After eight minutes, the carrier fluid emerging from the outlet tube connected to the valve 110 at a rate of one drop every two minutes was collected. Each drop was separately collected in a sterile McCartney bottle containing 10 ml of sterile 0.1% peptone water and the number of colony-forming units contained in each drop (0.4 ml) of carrier fluid emerging from the column was determined separately for each of the two microorganisms. At the end of the experiment, the standing wave was extinguished and the contents of the tube 101 were flushed out.

To obtain counts of the bacteria and the yeasts contained in each of the McCartney bottles, the following pour plate techniques were used employing Plate Count Agar (Difco) and a modified Potato Dextrose Agar (Oxoid) respectively.

At 25° C., the Plate Count Agar (PCA) had a Ph of 7.0±0.2 whereas the potato Dextrose Agar (PDA) had its normal working pH of 5.6 reduced to 3.5±0.2 at 25° C. by the addition of 1.0 ml of 8.5% Tartaric acid to 100 ml. of Agar.

Previous tests confirmed that the PCA plates incubated at 37° C. for 24 hours allowed the growth of *Serratia marcescens* sufficiently to obtain a complete colony count, while no yeast colonies appear in that time and at that incubation temperature.

The PDA plates incubated at 30° C. for 3 to 4 days allowed colonies of yeast only to develop because the low pH of the medium suppressed all growth of the *Serratia marcescens*.

Two series of Petri dishes were therefore prepared in which to carry out a standard decimal dilution pour plate technique. Samples of the mixed organisms in each of the McCartney bottles column were used to prepare a set of both PCA plates and PDA plates down to a dilution factor of $10^{-7}$.

The colonies which developed on the plates were counted after incubation at temperature and times given above. Any appropriate counting method can be used, but in this example the counts on the plates having large numbers of colonies were given greater statistical weight than the count of the next highest dilution.

Thus, for example, a $10^{-4}$ plate having 300 colonies and the $10^{-5}$ plate having 25 colonies would counted as:

300+25 =325 divided by 1.1 to give $295 \times 10^4$ or $2.95 \times 10^6$.

Results

Using standard microbiological methods, the viable counts of the yeasts and the bacterium in the mixed population as injected into the column were:

*Serratia marcoscens* $4.13 \times 10^8$ organisms per ml. and,
*Torulopsis bombicola* $5.57 \times 10^7$ organisms per ml.

The ratio of *Serratia* to *Torulopsis* thus being 7.4:1

The number of *Serratia marcescens* and *Torulopsis bombicola* colony-forming units found in each drop of carrier fluid emerging from the outlet of the column via the port 105 is shown in FIG. 6 plotted against time. Note that the highest concentration *Serratia marcescens* appears as a peak 4 minutes before the highest concentration of *Torulopsis bombicola* was reached.

The ratio of the counts of the bacteria and the yeast in each drop was calculated and the averages of successive ratios plotted against time as shown in (FIG. 7).

Referring to FIG. 7, the ratio of the bacteria to the yeast was always greater than the ratio (7.5:1) at which they were injected into the column and the maximum ratio reached was 80:1. The average ratio over the period during which the column was working was 24:1, nearly a three-fold enrichment.

The total number of bacteria injected was $16.5 \times 10^6$, while $11 \times 10^6$ were recovered from the outlet of the column while the standing wave was maintained and a further $5 \times 10^6$ were recovered subsequently while the column was flushed out. Thus all the bacteria subjected to the ultrasonic wave were recovered as viable, colony forming units after one hour of exposure, within experimental error.

The total number of yeast cells injected was $22 \times 10^5$ of which $5 \times 10^5$ were recovered from the outlet while the standing wave was maintained and $1 \times 10^5$ colony-forming units were recovered after the column was shut down and flushed out. The apparent loss is believed to have been due to the observed clumping of the yeast cells at the nodes of the standing wave, because these clumps were not completely broken down in the counting procedure and hence each colony-forming unit constituted a group of viable cells. Had the yeast cells been losing viability in the column, the ratio of the concentrations of the two microorganisms at 10 minutes and after 50 minutes operation would have been different. No such difference was observed.

The enrichment of the bacteria in the population emerging from the column was due to the greater nodal delay to which the somewhat larger yeasta cells were subjected to as they passed through the standing wave.

In the foregoing examples, the process involves separation of a mixture of particles into two groups. In the case of Examples 1 to 3 the ports 102, 103 are used to provide a continuous supply of feedstock while the port 104 is employed to establish a liquid flow down the column. Port 105 is opened intermittently to remove the particles of one separated group, otherwise it and the port 106 remain closed. In Example 4, a discontinuous process using the illustrated apparatus was performed in which particle size groups were separated by bringing them to the port 105 spaced in time, and in principle such temporal separation can bae employed if more than two groups are to be differentiated. In this case only the ports 102 and 105 are open continuously, the port 103 being used simply for initial injection of the sample. The apparatus can also be operated to provide further degrees of separation in a continuous standing wave, and by opening valve 111 to permit a flow through port 106, which has not been employed in any of the examples so far described.

Consider the circulating flow from the pump 119 going through the column from port 103 to pot 102, port 106 being open and pump 131 drawing liquid from the column through port 106, pump 125 driving liquid into the column through port 104, and port 105 being open to receive the flow that passes to the top of the column. In the region between port 102 and 103, the relative velocity of the standing wave and the liquid counter-flow is so large that no particles are carried by the nodes of the standing wave. At the same time, the flow into the column through the port 104 produces a flow up the column to exit port 105 and a flow down the column to the ports 106 and 102, the relative rates being determined by the pump deliveries and/or the openings of the valves associated with the ports. The flow through the port 104 is established such that the liquid flows from port 104 to port 106 with a velocity less than the flow velocity between ports 103 and 102. Because liquid is drawn off at the port 106, the flow velocity from port 106 to port 103 is lower still.

Thus, at the region opposite the port 103 particles are picked up by the nodes of the standing wave as the relative velocity between the wave and the liquid changes from the relatively high value between ports 102 and 103 to the relatively low value between ports 103 and 106. Above port 106, the downward liquid velocity increases again, but is not so great as to cause all the particles to be shed from the standing wave. Thus, in accordance with their characteristics, one group of particles will continue up the column with the standing wave but the remainder, being less firmly attached to the nodes, will leave the column with the flow through the port 106. That group of particles continuing upwards past port 106 are removed from the column by the flow through the port 105.

It will be noted that in this method of operation two distinct counterflow systems operate in two successive portions of the column, so that of the particles drawn off from the circulating flow from the tank 122, two separate groups are formed. It will be clear from this example that apparatus according to the invention may comprise further liquid inlet and/or outlet ports along the length of the column to establish a series of different flow velocity regimes, thereby to increase the number of fractions into which a mixed group of particles is separated in a continuous process.

Separation of different groups of particles that are differently influenced by the standing wave can also be obtained by controlling the intensity of the standing wave. Thus, if a mixed sample of particles is injected into a flow of fluid in a column in which a standing wave pattern is established, as already described, it is possible to select an initial acoustic energy level at which all but a first group of weakly influenced particles are retained at the nodes. This first group is carried along in the liquid flow and can be collected separately from the remainder of the particles. The energy level of the standing wave is then decreased to allow a further fraction of the particles to be released and collected, and the process can be repeated to collect further fractions. It will be clear that it is also possible to control separation by a combined variation of the standing wave intensity and the relative movement between the carrier fluid and the standing wave pattern.

The operation of the processes described may be driven by both acoustic forces and Stokes forces which are relatively large compared with the gravity forces on the particles. It will be understood, therefore, that the references to a column in this specification will include arrangements in which the column is disposed horizontally or obliquely.

An example of a cross-flow apparatus according to the invention, in which fine particles are segregated into three different groups according to their diameter is described below with reference to FIGS. 8 and 9. A chamber 202 fabricated from polymethylmethacrylate with front and back plates 204, 206 each 6mm thick defining between them a working column 208 3 mm deep extending between parallel side walls 210. At the inlet to the chamber there is a 25 micron sieve plate 212, and at the opposite end of the chamber outlets are provided by six identical converging sections 214 which each end in a small bore outlet tube 216. The working length between the inlet and the end sections is 24mm. At the inlet of the chamber, immediately downstream of the sieve plate 212, is an inlet tube 218 through which a mixture of particles to be separated is introduced into the chamber.

The chamber is mounted vertically with the outlets uppermost in a larger container (not shown) where it is immersed in a carrier fluid (ISOTON II-Coulter Electronics Limited) which fills the container and provides acoustic coupling for two ceramic (barium titanate) transducers 220, 20 mm high × 10 mm deep, operating at a frequency of 4.36 MHz. The transducers are mounted about 260 mm apart facing each other and are both coaxial with the centre line of 20 mm high acoustic windows 222 in the opposite side walls 210 of the chamber. The windows have a thickness equal to an integral number of half wavelengths of the outputs from the transducers, thus maximising acoustic transmissions into the working column 208. Other parts of the chamber walls have thicknesses which are of numbers of quarter wavelengths in order to provide maximum sound reflection, thus shielding areas inside the cell from the standing wave.

The outlet ports are connected by small bore tubing to a peristaltic multi-channel pump (Watson-Marlow 202U/AA10) (now shown) which draws carrier liquid uniformly from the larger container into the chamber 208 from where uniform flows are drawn throug the outlet sections 214.

The amplitudes of both transducers 220 are matched such that, in the absence of the chamber 202 the energy density at the centre of the larger container on the common axis of the transducers is 2.5 J/m$^3$.

A mixture of polystyrene and divinylbenzene microspheres having a concentration of about $2.10^7$ ml was pumped through the inlet tube 218 at 0.0112 ml per minute while 0.148 ml per minute was pumped out of each of the six outlet tubes 216, giving a mean liquid flow velocity in the working volume of the chamber of 12.3 mm per minute. As in preceding examples, the standing wave was caused to drift, the movement being to the right as seen in FIG. 8 (i.e. away from the side wall at which the particles are fed into the chamber), at 24.2 mm per minute.

Figure 10:
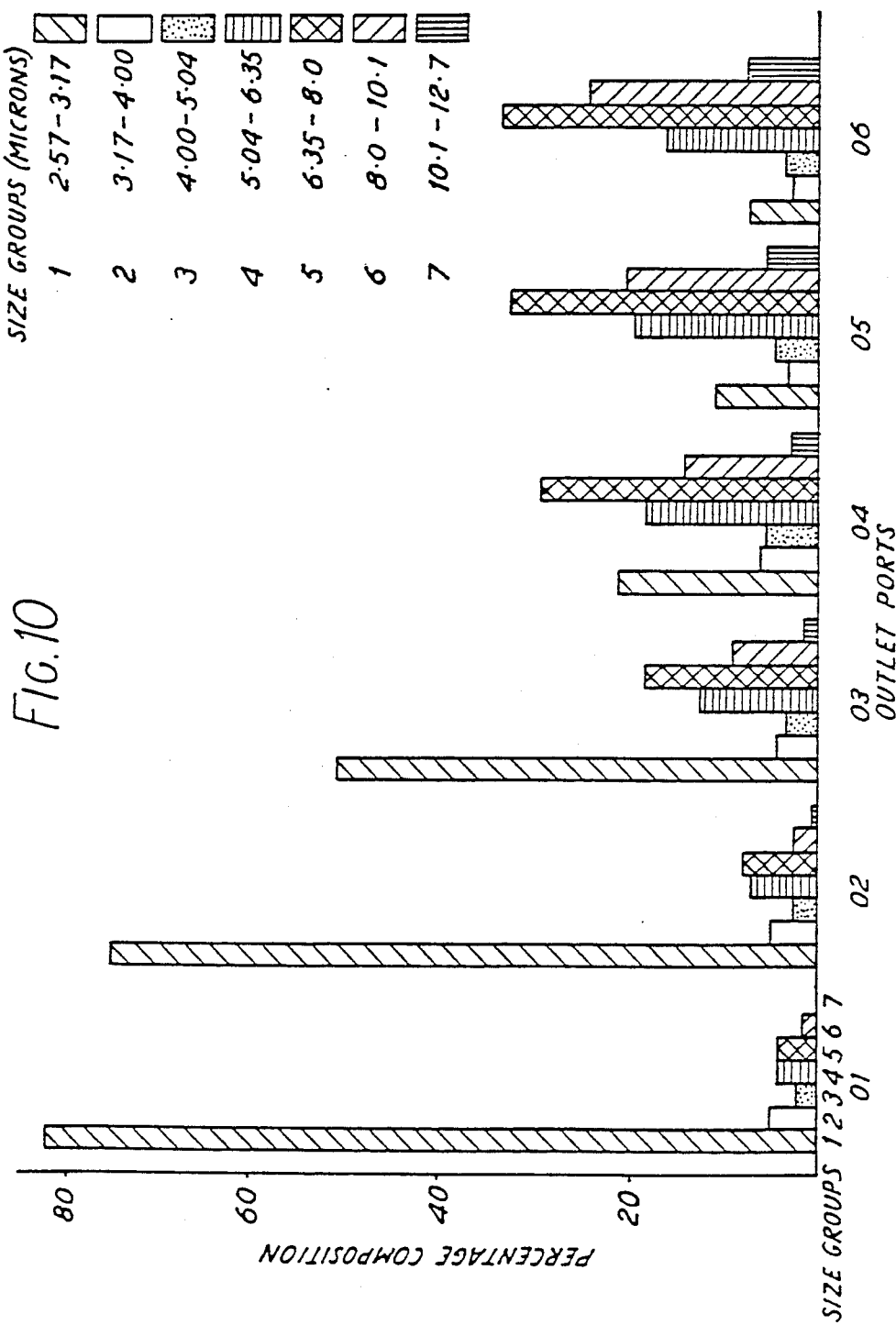
FIG. 10 is a bar chart illustrating results obtained in the use of the apparatus of FIGS. 8 and 9, and, FIG. 11 is a diagrammatic illustration of a further form of apparatus according to the invention.

The composition of the particle population appearing at the outlet tubes is shown in FIG. 10 in a grouped histogram of percentage composition in each of seven size groups (2.5 to 12.7 microns) for each port. Table 4 below also shows the percentage composition of the particle population going through the chamber inlet tube.

TABLE 4

| Size Group: mean diameter (microns) | Particles entering inlet | Particle Population Leaving Ports | | | | | |
|---|---|---|---|---|---|---|---|
| | | 01 | 02 | 03 | 04 | 05 | 06 |
| 2.85 | 44.3 | 82 | 75 | 51 | 21.4 | 11.6 | 7.4 |
| 3.59 | 10.6 | 5.0 | 4.9 | 4.6 | 6.6 | 3.5 | 3.2 |
| 4.52 | 4.6 | 2.0 | 2.4 | 3.5 | 5.8 | 4.9 | 3.9 |
| 5.70 | 8.9 | 4.7 | 7.1 | 12.7 | 18.6 | 19.8 | 16.7 |
| 7.18 | 15.6 | 4.7 | 7.8 | 18.5 | 29.4 | 32.6 | 33.8 |
| 9.05 | 11.3 | 1.2 | 2.4 | 8.1 | 14.7 | 21.0 | 24.6 |
| 11.4 | 3.8 | 0.2 | 0.3 | 1.2 | 3.0 | 5.7 | 8.1 |
| 14.3 | 0.9 | 0.0 | 0.0 | 0.3 | 0.4 | 0.8 | 1.7 |

Figure 11:
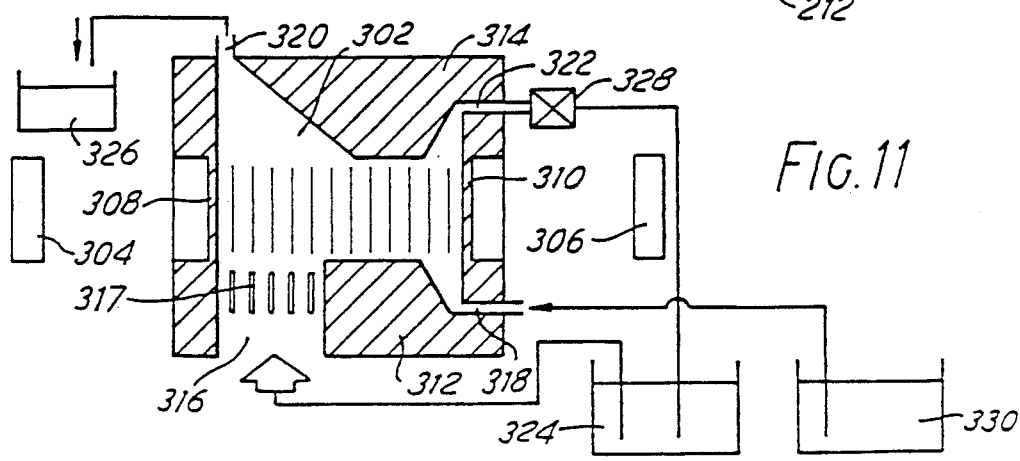

FIG. 11 illustrates a further apparatus according to the invention in which separation of a selected type of particle suspended in a liquid is effected by the action of an ultrasonic standing wave while the liquid flows transversely through the standing wave. The apparatus comprises a chamber 302 having a relatively shallow depth similarly to the example of FIG. 9. Respective ultrasonic transducers 304, 306 at opposite ends of the chamber direct their outputs coaxially through windows 308, 310 substantially in the manner described in the preceding example to provide a drifting standing wave that occupies essentially the total cross-section of the chamber in an intermediate region between opposite side walls 312, 314. At opposite ends of the intermediate region in one side wall are respective entry ports 316, 318 and in the other side wall respective exit ports 320, 322 are similarly arranged, so that the liquid flow between the entry and exit ports must pass through the standing wave.

The apparatus is intended to separate one type of particle from a mixture of particles in a liquid flow supplied from a container 324 to the first entry port 316, where guide vanes 317 ensure a parallel streamline flow, the standing wave being adapted in this instance to allow that one type to pass through it in the liquid flow to the opposite exit port 320 from which the particles are then collected in a discharge container 326. The remaining particles in the liquid flow entrained by the drifting standing wave are carried to the end window 310. At intervals the particles collected on the window are returned to the container via the other exit port when a valve 328 in return line is opened. The second entry port 318 receives from a reservoir 330 an additional flow of liquid free of particles to establish in the zone of action of the standing wave a liquid flow counter to the direction of drift of the wave, so assisting the delivery to the first exit port 320 any particles of said one type that may have been carried along with the particles attached to the standing wave.

As one example, the container 324 may hold a plant cell culture in a liquid medium, the apparatus being employed to remove damaging microorganisms therefrom. Continuous inputs from the container 324 and the reservoir 330 are pumped through the respective entry ports 316, 318, the main flow being from the container 324, e.g. the flows through the respective ports being in the ratio 5:1. The standing wave characteristics are chosen so that the plant cells are attached strongly to the nodes but any microorganisms present are unaffected or are only weakly attached to the nodes. Because of the very large difference in size it is possible it differentiate thus between the plant cells and a spectrum of different microorganisms. The microorganisms are accordingly carried by the liquid flow through the standing wave to be discharged in a continuous flow of liquid through the outlet port 320 to the discharge container 326. Microorganisms that happen to be initially attached to the nodes of the standing wave are removed by the liquid flow from the other inlet port 318 which will provide a small but positive counterflow to the drift of the standing wave. The plant cells carried across the chamber by the standing wave collect on the window 310 and by intermittently opening the valve 328 and simultaneously admitting a much higher flow of liquid from the reservoir 330 the cells will be washed out of the chamber back to the container 324.

The method of operation is so controlled that the volume of liquid in the container 324 is replenished from the reservoir 330, and the sequence can be repeated to purify the contents of the container. In general, it is of course not essential to achieve complete separation. It is sufficient simply to control the microorganism pupulation in the container 324 so as to maintain the healthy growth of the plant cells in it.

Another possible use for the apparatus is for the collection of a blood fraction, such as platelets. Diluted blood is admitted through port 316, the standing wave characteristics being so adjusted that only the platelets are carried by the liquid flow to the exit port 320, the remaining particulate matter being collected on the window 310. Periodic removal of this collected material is obtained by a washing flow of undiluted blood from the reservoir 328 which also introduces further platelets into the separation.

Figure 8:
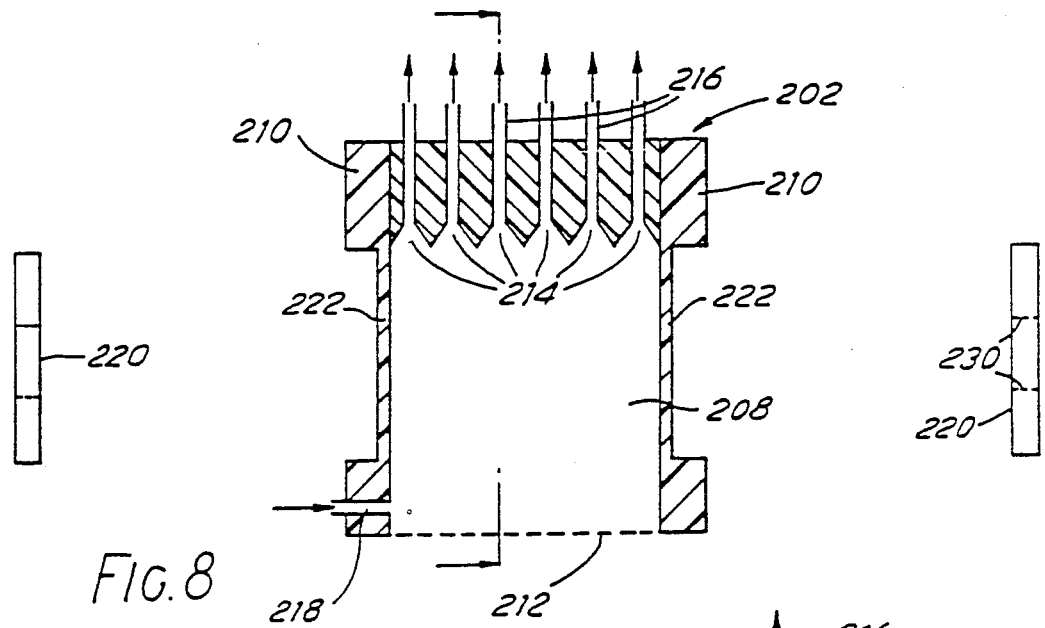
FIGS. 8 and 9 are diagrammatic cross-sections, taken at right-angles to each other of another form of apparatus according to the invention.
Figure 9:
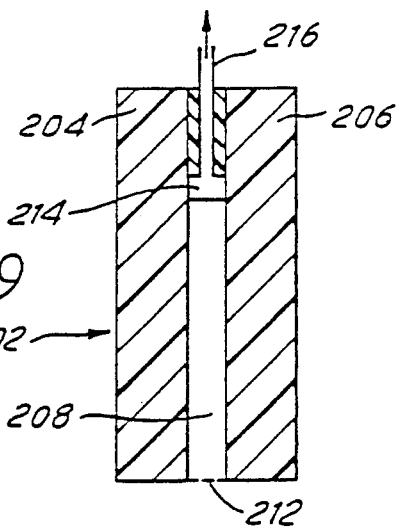

In a modified arraangement according to the invention that may be applied particularly simply to apparatus such as that shown in FIGS. 8 and 9 or FIG. 11, in which the carrier liquid flows transversely through the standing wave, it is possible to establish two or more standing waves in different flow regions so that the liquid passes successively through each standing wave. The apparatus of FIGS. 8 and 9 or FIG. 11 for example may have the single pair of transducers replaced by a number of pairs of coaxial transducers (three pairs of transducers being indicated by the broken lines 230 in FIG. 8) that establish a corresponding number of parallel standing waves. The output characteristics of each pair of transducers may be individually controlled to give a different form of separation. By these means it is possible to achieve greater descrimination between a number of different particle types. Of course, in all cases it is possible to replace the individual transducers of a pair by arrays that are driven together to operate as single sources, e.g. to increase the width of the standing wave in a convenient manner, so as to increase descrimination or to handle larger mass flows.

Reference has been made already to varying the frequency of the ultrasonic outputs to control the separation process. In general, the outputs will be transmitted through windows to a liquid-filled space in which the standing wave performs the separation process and the thickness of a window is related to the wavelength of the output. A window of given thickness will, however, transmit ultrasound at a number of frequencies if those frequencies bear a simple relation to the window thickness in terms of an integral number of half wavelengths. it is thus possible to change the frequency substantially in order to establish a different internodal distance in the standing wave so that the selectivity of the standing wave is changed.

Such a technique can be applied to any of the apparatus illustrated, but as an example, reference will be made to FIG. 11 in the use of the separation apparatus with a plant cell culture containing single cells and various clumps of cells. As already described, the culture is pumped from the vessel 324 into port 316. The transducer outputs, initially at a frequency of 16 MHz, establish a uniform wave drift as the flow of fluid through the port 316 into the standing wave is established. At that frequency the internodal distance in water (45 microns) is such that only single cells will be carried to the window 306 and thus to port 322, while all cell clumps emerge from the port 320. If the frequency is changed to 8 MHz, the internodal distance is 90 microns, and only medium and large clumps are carried to the port 320. At 4 MHz, only large and very large clumps reach the port 320, a further halving of the frequency to 2 MHz results in an internodal distance of about 360 microns so that only the largest clumps, with a size of about 0.25 mm upwards, are carried ot the port 320.

I claim:

1. An apparatus for separating one or more particle types carried in a fluid flow comprising a flow chamber, spaced ultrasonic energy sources arranged to establish a pattern of nodes therein by interference between their outputs defining a standing wave, an axis of the standing wave pattern extending perpendicular to the nodes means for controlling said sources so as to produce drifting of the standing wave along the axis of the wave pattern, fluid inlet and outlet means for the liquid flow carrying said particles, said inlet and outlet means being disposed relative to said standing wave such that the fluid in the chamber flows through said standing wave transversely to the axis thereof, the outlet means comprising at least two openings that are spaced in the direction of said axis whereby particles of a chosen type, in dependence upon their displacement relative to the liquid imposed by the standing wave energy, are delivered to a predetermined opening.

2. Apparatus according to claim 1 having respective pairs of ultrasonic sources establishing a plurality of standing waves through which the fluid is arranged to flow successively in its passage to the exit means.

3. Apparatus according to claim 1, wherein means are provided to cause the fluid to flow in a generally parallel streamline flow at least in the regions in which it is influenced by the standing wave.

4. A method of separating one or more particle types present in particulate matter in a liquid column, said column having a longitudinal axis and a standing wave being established in said column by interference between the outputs of spaced ultrasonic energy sources, said standing wave having an array of wave fronts in the column extending transversely of said longitudinal axis, said separation being obtained by controlling at least one of a series of parameters consisting of the rate of liquid flow, the rate of drift of the standing wave along the column, the intensity of the standing wave, and the frequency of the standing wave, a separated group of particles being collected in a chosen region of the column, said chosen region having an exit station through which said separated group of particles is removed by directing a flow of liquid into the region to entrain the particles through said exit station.

5. A method according to claim 4, wherein successive groups of different particle types are retained in the column for different periods of time to be removed sequentially through said exit.

6. A method according to claim 4, wherein a non-acoustic force field acts on the particles to promote said separation in the standing wave.

7. A method according to claim 4, wherein said spaced energy sources are operated at ultrasonic freqeuncies of at least 100 kHz.

8. A method of separating one or more particle types present in particulate matter in a liquid column, said column having a longitudinal axis a standing wave being established in said column by interference between the outputs of spaced ultrasonic energy sources, said standing wave having an array of wave fronts in the column extending transversely of said longitudinal axis, said separation being obtained by controlling at least one of a series of parameters consisting of the rate of liquid flow, the rate of drift of the standing wave along the column, the intensity of the standing wave, and the frequency of the standing wave, wherein a continuous flow of liquid is passed through the column between spaced entry and exit ports thereof, said at least one separated particle type being removed whilst suspended in the flow of liquid through said exit port.

9. A method according to claim 8, wherein the column has a plurality of exit ports and more than one particle type is separated, each said particle type being extracted through a respective exit port.

10. A method according to claim 8, wherein respective liquid flow systems with different velocities are established in different parts of the length of the column.

11. A method according to claim 8, wherein a non-acoustic force field acts on the particles to promote said separation of the standing wave.

12. A method according to claim 8, wherein said spaaced energy sources are operated at ultrasonic frequencies of at least 100 kHz.

13. Apparatus for separating at least one particle type present in particulate matter suspended in a liquid, comprising:

a column for said liquid having at least a single first kind of station for entry and at least a single second kind of station for exit;

means for directing the liquid and said matter into the column and for establishing a continuous flow of liquid therethrough, the column having a longitudinal axis and being provided with a plurality of one of said kinds of stations at spaced positions along said axis for establishing different velocity flow regions for said flow of liquid over respective parts of the length of the column;

spaced ultrasonic energy sources for directing respective wave outputs into the liquid column to generate by interference between their outputs a standing wave with an array of wave fronts in the column extending transversely of said longitudinal axis; and means for performing at least one of a series of regulating operations, consisting of (i) controlling the amplitudes of the outputs of the two sources so as to vary the intensity of the standing wave, (ii) controlling the frequency of the outputs of the two sources so as to vary the wave length of the standing wave, and (iii) controlling the relative phase of the two outputs so as to hold the standing wave fixed or to produce an adjustable rate of drift of said standing wave along the column, whereby said at least one particle type is separated from the liquid.

* * * * *